United States Patent [19]

Djabbarah

[11] Patent Number: 4,589,276

[45] Date of Patent: May 20, 1986

[54] METHOD AND APPARATUS FOR DETERMINING EFFECTIVENESS OF FOAMANT IN POROUS MEDIA

[75] Inventor: Nizar F. Djabbarah, Richardson, Tex.

[73] Assignee: Mobil Oil Corporation, New York, N.Y.

[21] Appl. No.: 680,865

[22] Filed: Dec. 12, 1984

[51] Int. Cl.$^4$ ............... G01N 13/00; G01N 33/28
[52] U.S. Cl. ........................... 73/60.1
[58] Field of Search ...................... 73/60.1

[56] References Cited

U.S. PATENT DOCUMENTS 1,866,296  7/1932  Christmann ............... 73/60.1

OTHER PUBLICATIONS

Prigorodov, V. N. *Apparatus for Studying the Foam—Forming Properties of Liquids*, In Industr. Lab., vol. 35, No. 10, pp. 1552–1553, Oct. 1969.

*Primary Examiner*—Stewart J. Levy
*Assistant Examiner*—Joseph W. Roskos
*Attorney, Agent, or Firm*—A. J. McKillop; Michael G. Gilman; George W. Hager, Jr.

[57] ABSTRACT

The foaming characteristics of a foamant to be used in the recovery of oil from a subterranean oil-bearing formation by carbon dioxide foam flooding, are determined by passing carbon dioxide through a sample of the foamant in a test cell containing a porous medium under pressure conditions simulating reservoir conditions and measuring the quantity of foam formed. The pressure drop along the cell is also monitored in order to indicate the resistance to gas flow imposed by the foam.

8 Claims, 2 Drawing Figures

METHOD AND APPARATUS FOR DETERMINING EFFECTIVENESS OF FOAMANT IN POROUS MEDIA

FIELD OF THE INVENTION

This invention relates to a method and an apparatus for determining the foaming characteristics of a foamant solution and the characteristics in porous media, especially the stability, of the foam formed using such a solution. The invention is particularly applicable to the determination of foaming ability and foam stability with foamants used in carbon dioxide foam flooding processes used in the enhanced recovery of oil from subterranean, oil-bearing formations.

BACKGROUND OF THE INVENTION

In the recovery of oil from subterranean, oil-bearing formations, it is usually possible to recover only a limited proportion of the original oil present in the reservoir by the so-called primary recovery methods which utilize the natural formation pressure to produce the oil through suitable production wells. For this reason, a variety of supplementary recovery techniques have been employed, directed either to maintaining formation pressure or to the displacement of the oil from the porous rock matrix. Techniques of this kind have included formation pressurization, thermal recovery methods such as steam flooding and in situ combustion, water flooding and miscible flooding techniques.

One of the flooding techniques which has been investigated is carbon dioxide flooding and this is considered to be a method of substantial promise. In the carbon dioxide flooding technique, a slug of carbon dioxide is injected into the formation to mobilize the oil and permit it to be displaced towards a production well at an offset from the injection well. Carbon dioxide is not miscible in crude oil under normal conditions because the pressure at which it becomes miscible with most reservoir oils is generally greater than about 7,600 kPa (about 1,100 psia). However, under supercritical conditions, usually of high pressure, carbon dioxide acts as a solvent and in certain reservoir situations has a great advantage over more common fluids as a displacement agent. Even under conditions where the carbon dioxide is not wholly effective as a solvent for the oil, recovery may be improved by taking advantage of the solubility of carbon dioxide in the oil, causing a viscosity reduction and a swelling of the oil, which leads to increased recovery. These effects have been utilized at pressures much lower than the miscibility pressures for carbon dioxide for oil. Processes using carbon dioxide as a recovery agent are described, for example, in U.S. Pat. Nos. 3,811,501, 3,811,502, and 4,410,043.

One problem which arises from the use of carbon dioxide as a flooding agent is that it is much less viscous than oil or water and the result of this is that the injected fluid does not displace the oil uniformly. Instead, the carbon dioxide moves faster in some regions and directions than others and "viscous fingers" are formed through which most of the injected fluids flow. Some of these fingers may arrive prematurely at the production well, lowering the effectiveness of both the injected carbon dioxide and of the production pumping capacity.

Several general methods have been proposed for controlling the mobility of carbon dioxide when used as a flooding agent so as to maintain the desired profile in the front between the slug of carbon dioxide and the oil in place in the reservoir. In general, the methods used or proposed for the control of frontal instability entail the increase of the flowing pressure gradient behind the front, that is, a decrease in the displacing fluid's mobility. An initial proposal to decrease the effective mobility of the displacing fluid, so as to increased the pressure gradient in the region it occupied was to add water to the injection fluids in the process known as WAG, or water alternated with gas. Although this procedure has been adopted in a number of applications, there are problems with its effectiveness. First, the injected water may prevent the oil forming good contact with the displacement fluid and second, the gravity segregation of the water and gas results in the more dense water flowing in the lower zone and the less dense carbon dioxide preferentially flowing in the upper zone of the reservoir so that the potential advantages of the process were vitiated. A second proposal has been to use a foam-like dispersion of carbon dioxide in a surfactant solution because composite fluids of this kind would have a decreased mobility through porous rock, apparently as a consequence of the formation and migration of the aqueous films in which most of the water present in the foam is transported. These films would separate the carbon dioxide into cells, increasing its resistance to flow in the porous medium. It has been known for some time that a surfactant stabilized foam of gas and water has a very low mobility to flow through porous media such as the porous rock matrices of subterranean, oil-bearing formations. Because the foam is a composite fluid with a structure comparable in size to the average pore size of the rock matrix, the mobility in the rock cannot be assumed to be capable of calculation as the ratio of rock permeability to a fluid viscosity. Despite this difficulty, however, the mobility reduction has been measured under reservoir conditions in the laboratory and measurements utilized for prediction of behavior in the field. However, the methods previously used for determining the foaming ability of a foamant solution and the stability of the foam generated have been inconvenient and have required correlations and assumptions in relating conditions measured in the laboratory with those which are likely to exist in the reservoir.

A number of tests have been proposed in the past, including the standardized method known as the "Ross Miles Technique" described in "Foaming Agents: Cure for Waterlogged Gas Wells" Dunning, H. N. et al., Pet. Eng. November 1959, pp b28–b33. This test was, however, envisaged merely as a screening test and the requirements of mobility control in carbon dioxide floods have imposed other constraints on the foam generation than simply that they must be producible at ambient conditions. These constraints include chemical compatability with carbon dioxide and, to some extent, with crude oil. Tests of foam generation and stability under reservoir conditions of temperature and pressure are therefore needed. While pressure is apparently innocuous to the mobility reduction properties of foams in porous media, the high pressures which are prevalent in reservoirs may impose a different environment which may alter foaming characteristics; for this reason, pressure is a significant consideration and requires to be taken into consideration in any test for the utility of a foamant. Any test for the suitability of a foamant under practical conditions therefore requires its effectiveness to be directly examined. Thus, measurements should be made of mobility reduction in different porous media.

SUMMARY OF THE INVENTION

I have now devised a method and an apparatus which can be used to determine the foaming ability of a foamant solution and the stability of the foam generated from the solution under dynamic flow conditions in a porous medium with reservoir fluids and simulated reservoir temperatures and pressures.

According to the present invention, the apparatus for determining the properties of a foamant in a porous medium comprises a cell packed with a porous medium in which the foamant is to be tested, means for maintaining a predetermined gas pressure within the cell, means for injecting a predetermined quantity of carbon dioxide into the cell under the predetermined pressure in the presence of the foamant, means for monitoring the pressure gradient along the cell and means for determing the advance of the generated foam along the length of the cell.

The method according to the present invention comprises injecting carbon dioxide at a predetermined rate into the cell packed with the porous medium in the presence of the foamant and under the predetermined pressure, monitoring the advance of the foam in the cell until it reaches a constant height and measuring the height and the pressure differential along the cell.

DRAWINGS

In the accompanying drawings:

FIG. 1 is a simplified schematic of an apparatus which may be used for measuring the foaming ability and stability of a foamant in a porous medium, and FIG. 2 is a simplified schematic of an alternative form of apparatus.

DETAILED DESCRIPTION

The term "foamant" has been used elsewhere and is used in this specification to refer to a material which is capable of forming and stabilizing a foam from a mixture or emulsion of water with a displacing gas, in this case, carbon dioxide. Foamants of this kind are also referred to as foaming agents but the term foamant is preferred by analogy to surfactant as a generic term for surface active agents. Foamants are generally the same kind of surfactant-viscosifier materials which enable a visible foam to be produced from the water and the displacing gas. Generally, these materials will enable to foam to be produced in an open container away from the confines of a porous medium and it is the ability of these foamants to produce a foam under reservoir conditions that the present invention is directed. There are many chemicals which have been tested for their suitability as foamants and they are generally surfactants, usually of the anionic type although cationic and nonionic surfactants may also be used, as well as mixtures of various surfactants. Regardless of the nature of the foamant, however, its potential for use in carbon dioxide foam flooding operations may be evaluated by the present method and apparatus. Specific foamants include, for example, anionic surfactants such as sodium lauroyl sulfate, sodium dodecyl sulfate, lauroyl sulfate, potassium laurate, sodium dodecyl benzyne sulfonate, ethoxylated alcohol derivatives such as the ammonium salt of linear alcohol ethoxylate sulfate commercially available under the trademark Alipal CD-128 (GAF) and potassium oleate, cationic surfactants such as dodecyl ammonium chloride, hexadecyl trimethyl ammonium bromide and nonionic materials such as 2-amino-2-methyl-1-propanol, 2-amino-1-butanol, 2-amino-2-methyl-1-3-propane diol, tris (hydroxymethyl amino) methane, lauryl alcohol and ethoxylated alcohols such as nonyl phenoxy poly (ethyleneoxy) ethanol, e.g., the commercially available material with nine ethyleneoxy units sold under the trademark Igepal CO-630 (GAF).

Figure 1:
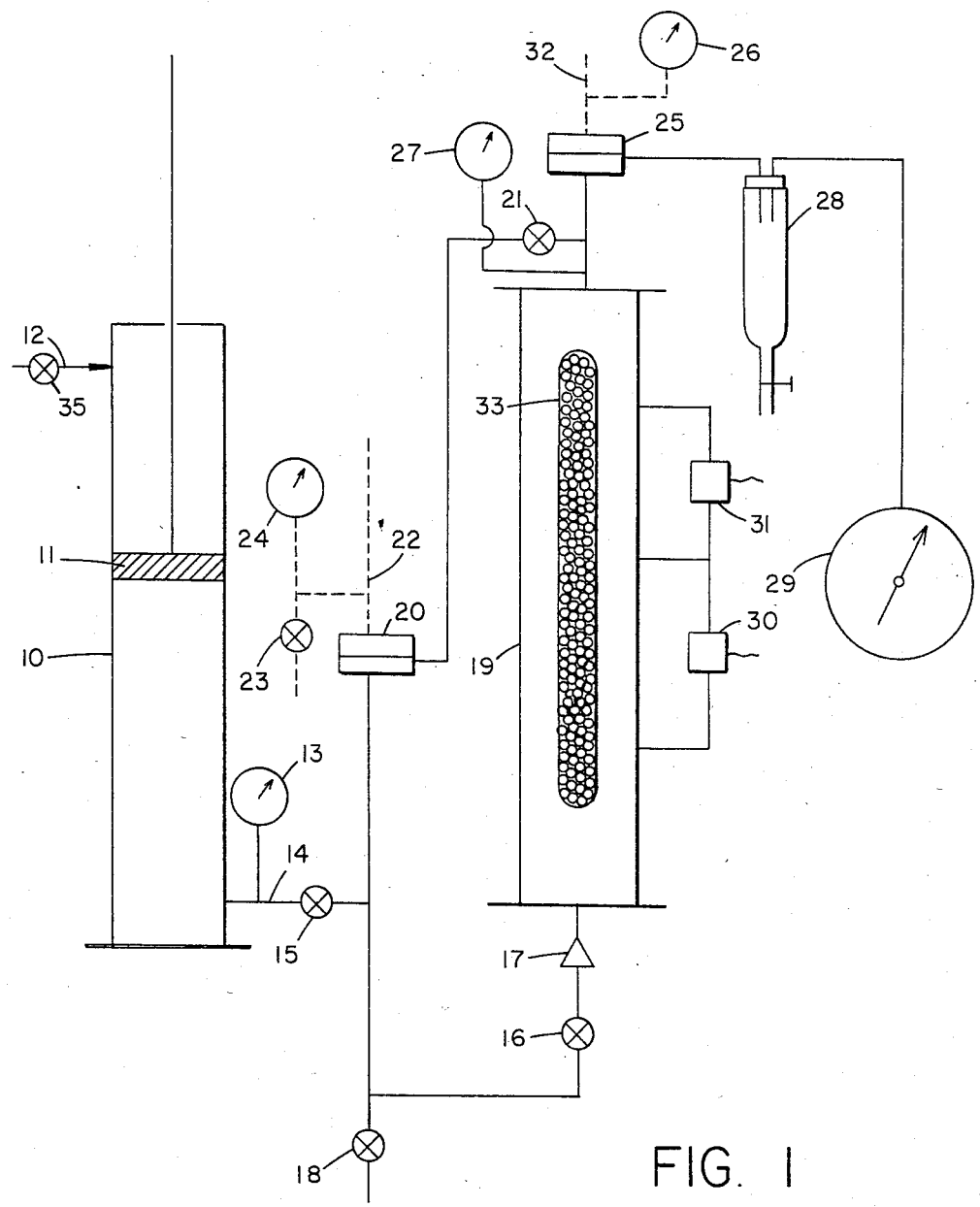

The apparatus shown in FIG. 1 comprises a carbon dioxide transfer vessel 10, suitably a cylinder of stainless steel of about 1,000 ml. capacity, fitted with a displaceable piston 11 separating the upper portion from the lower portion. A water inlet 12 is connected to a pump (not shown) by way of inlet valve 35 for admitting water at a controlled rate to the upper portion of the transfer vessel above the piston. The lower portion of the transfer vessel is connected by means of conduit 14 to the carbon dioxide main valve 15, with pressure gauge 13 being connected in a branch conduit. From valve 15, the carbon dioxide line divides into two branches with the lower branch going to high pressure visual cell 19 by way of inlet valve 16 and check valve 17. The visual cell may typically be about 30 cm. high and of about 400–500 ml. capacity. Relief valve 18 is provided in a branch conduit. The upper branch passes to the upper end of the visual cell by way of back pressure regulator 20 and pressurizing valve 21. The opposite side of back pressure regulator 20 is connected to a regulated nitrogen source (not shown) by way of conduit 22, with the back pressure relief valve 23 and back pressure gauge 24 connected in side branches of the conduit. The upper end of visual cell 19 is also connected to a back pressure regulator 25 which is again connected to the regulated nitrogen source (not shown) by conduit 32 and fitted with back pressure gauge 26. The pressure over the top of visual cell 19 is indicated by pressure gauge 27 connected to the top of the cell. The remote side of back pressure regulator 25 is connected to burette 28 which, in turn, is connected to a wet test gas flow meter 29. Differential pressure transducers 30, 31 are connected to branch conduits leading out of visual cell 19 to monitor the pressure differentials between axially spaced locations along the visual cell. The outputs of these transducers may be monitored by suitable meters (not shown) connected to them. In order to ensure that determinations are made under controlled temperature conditions, the apparatus may be contained in a thermostatically controlled air bath (not shown).

In a typical procedure for measuring the foaming ability of a foamant and the stability of the foam which it produces under reservoir conditions, the high pressure visual cell is first filled with a porous medium which preferably approximates the reservoir medium. However, for many tests, an artificial medium of known wettability characteristics may be used and for this purpose, glass beads of approximately 3 mm. diameter may be used since the objective is to simulate reservoir conditions rather than to provide an exact replication of them. The oil may be chosen to simulate reservoir oil in order to simulate conditions as closely as possible. Recombined reservoir oil may be used.

The characteristics of the foamant are determined by first, supplying sufficient carbon dioxide to transfer vessel 10 under piston 11. The carbon dioxide is then allowed to reach thermal equilibrium, after which the vessel is pressurized by admitting water through inlet 12 so that the carbon dioxide pressure, as indicated by pressure gauge 13, is equal to the desired test pressure.

This pressure should preferably conform to the pressure in the reservoir under which the recovery operations will be carried out. With valves 15, 16, 18, 21 and 23 shut, high pressure visual cell 19 is packed with the desired packing and the top and bottom closure plates secured. A predetermined volume of solution, for example, 50 ml., which contains the foamant under test is placed inside the cell and the cell is then sealed. The differential pressure transducers 30, 31 and the cell pressure gauge 21 should, at this time, read zero.

The nitrogen sides of each of the two back pressure regulators 20 and 25 are then loaded with sufficient nitrogen pressure that pressure gauges 24 and 26 readings are equal to the test pressure plus the pressure drop across the back pressure valve diaphragms.

The visual cell is pressurized by slowly and carefully opening main valve 15 followed by valve 21, after which the $CO_2$ is charged into the visual cell by admitting water to the upper side of the transfer vessel 10. This should be done gradually so that the pressure rise in the visual cell is not sudden. The cell pressurization is continued until the reading of visual cell pressure gauge 27 is equal to the desired test pressure. At this point, water injection is terminated and pressurizing valve 21 is shut.

In order to generate the foam in the test cell, inlet valve 16 is opened very slowly and additional water is admitted to the upper side of the transfer vessel 10. The water is admitted into the transfer vessel at a rate such that the advance of the carbon dioxide into the visual cell is equal to that encountered in the flooding operations under consideration, for example, about 15 to 30 centimeters per day. The flow rate is monitored by monitoring movement of piston 11 in transfer vessel 10 and checked by the use of gas flow meter 29. Any liquid passing out of the cell is collected in burette 28 in which its volume may be measured. As the carbon dioxide bubbles through the foaming agent at the bottom of the test cell, foam is generated. The advance of the foam up the column of the packing can be monitored through the visual port 33 in the side of the test cell and measured, representing the advance of the carbon dioxide through the porous medium.

Finally, the foam height reaches a constant value which is proportional to the superficial gas velocity and from these determinations the unit of foaminess can be determined. Determinations may be based on either the injection or production rates of the carbon dioxide (as indicated by the transfer vessel and the gas flow meter, respectively) provided, of course, that a consistent basis is used. Because carbon dioxide is soluble in water and brine, the production rate of the carbon dioxide may not be equal to the injection rate during the course of the experiment.

The effect of oil on foaming ability and stability is determined by repeating the test with oil added to the foamant solution. If the oil is gas-free at the test temperature and pressure, a predetermined volume of oil is pipetted into the visual cell with the foamant solution, after which the cell is sealed. For example, 5 ml. of oil is added to the 50 ml. of foamant solution.

The foaminess of a foamant has been described, together with an apparatus for determining it in non-porous media under atmospheric conditions, in Trans. Farad. soc., 34, 634 (1938), Bikerman, J. J. and also, independently, in Bull. Chem. Soc. Japan, 13, 517 (1938), Sasaki, and further advances described by Dyankov, Chem. Abs. 37, 5299 (1943). The foaminess, F, is defined as the ratio of the foam height attained to the gas velocity:

$$F = \frac{h_o \text{ (cm)}}{u \text{ (cm. min.}^{-1})}$$

$$= \frac{h_o \text{ min.}}{u}$$

The foaminess therefore has units of time and is indicative of the foaming ability of the foamant and the stability of the foam which it generates under the selected conditions. For example, at a frontal advance rate of 0.0212 centimeters per minute (1 foot per day), and at a steady state height of the foam generated of 20 centimeters, the foaminess for the system would be:

$$F = \frac{20 \text{ cm.}}{0.0212 \text{ cm. min.}^{-1}}$$

$$= 945 \text{ min.}$$

For initial screening tests, a relatively fast advance rate may be selected so as to shorten the test duration; however, for final determinations, the advance should match that expected under actual reservoir conditions of operation.

The extent to which the foam increases the viscous resistance to gas flow may be determined by monitoring the differential pressure between pressure transducers 30 and 31 and determining the increase in flow resistance caused by the foam, in comparison to the resistance in the absence of foam.

The effect of matrix wettability on foaminess may be determined by conducting the experiment under different wettability conditions. This may be achieved, for example, by altering the wettability of the packing by various conventional techniques such as the one described G. L. Gaines, Jr. in J. Colloid Interf. Sci. 59 (3), 438 (1977) for altering the wettability of glass by first cleaning the glass by boiling in nitric-sulfuric acid solution, rinsing in distilled water, soaking overnight in 0.0025M NaOH solution, followed by another distilled water rinse and dyying in a convective oven. The dried beads may then be soaked for 30 minutes in a 2Δ solution of dimethylchlorosilane in carbon tetrachloride, followed by a final rinsing sequence with benzene, acetone and, finally, distilled water.

The experiment may be conducted in a physically scaled manner by choosing flow variables and packing medium geometry in such a manner that:

$$(Re)_{Experiment} = (Re)_{Reservoir}$$

where Re is the Reynolds number and is defined as $$Re = \rho\mu\beta/\mu\alpha$$

where
$\rho$ = gas density
u = superficial gas velocity
$\mu$ = gas viscosity
$\alpha\beta$ = characteristic constants Because the pressure in the test cell is maintained during the course of the experiment by the setting on back pressure regulator 25, the secondary back pressure regulator 20 with its associated equipment may be omitted if desired. When the initial pressure in the cell, as indicated by pressure gauge 27 is correctly set, pressurizing valve 21 is closed and the secondary back pressure regulator takes no further part in the procedure. It may therefore be omitted or, if desired, replaced by a simple, manually operated valve or a check valve.

Figure 2:
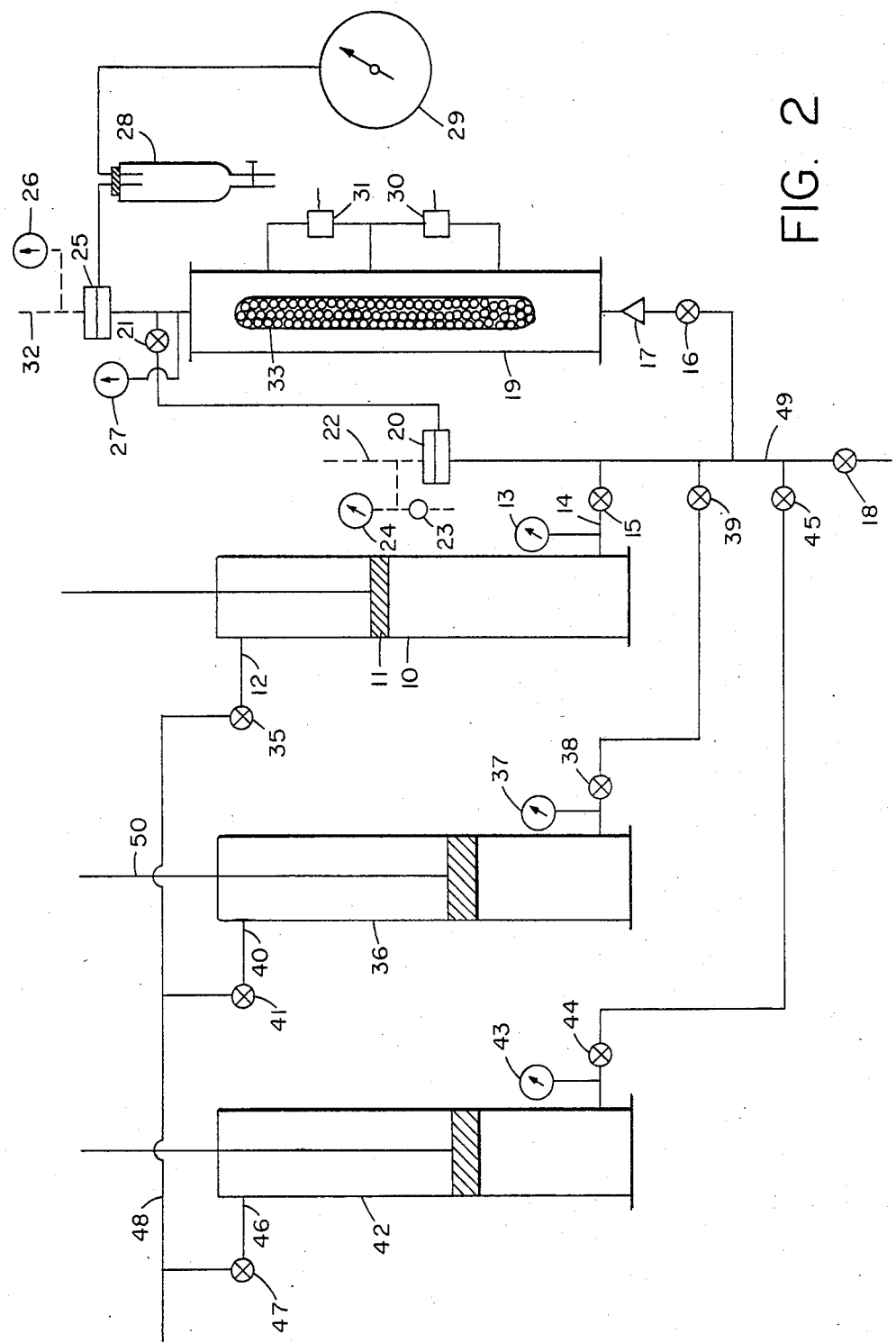

If the oil contains dissolved gases at the test conditions or if it is desired to conduct the experiment in a continuous manner, the arrangement shown in FIG. 2 may be used. It is similar to that shown in FIG. 1 except for two additional transfer vessels which are identical to the $CO_2$ tranfer vessel 10. The first is an oil transfer vessel 36. A water inlet 40 is connected to the water inlet line 48 of the $CO_2$ vessel and to the water pump (not shown) by way of valve 41. The lower portion of the oil transfer vessel is connected by means of conduit 38 to the oil main valve 39, with pressure gauge 37. From valve 39 the oil line is connected to the lines that lead to the upper and lower portions of the visual cell 19. A second transfer vessel 42 is for foamant solutions. A water inlet 46 is connected to the water inlet line which is also connected to the $CO_2$ and the oil transfer vessels. This common water pump arrangement ensures that the fluids are maintained at the same pressure so that flow can be switched from one fluid to another without causing any significant disturbance in the pressure of the system. The lower portion of foamant solution transfer vessel 42 is connected by means of conduit 44 to the foamant main valve 45, with pressure gauge 43 in the conduit. From valve 45 the foamant line is connected to a visual cell inlet manifold 49 which leads to visual cell 19 through valves 16 and 17, as in FIG. 1. The apparatus may be enclosed in a thermostatically controlled air bath (not shown) for controlled temperature operation.

After the visual cell is packed and sealed, each of the three transfer vessels 11, 36, 42 are supplied with their respective test fluids. At this point, all the valves in the system are shut and the fluids are allowed to reach thermal equilibrium. At this point, valves 35, 41 and 47 are opened and water is simultaneously admitted to the upper portions of the three transfer vessels so that the pressures of the fluids, as indicated by pressure gauges 13, 37 and 43, are equal to the desired test pressure. With all valves except 35, 41 and 47 shut, the visual cell is packed with the desired packing and the top and bottom closure plates are secured.

The nitrogen sides of each of the two back pressure regulators 20 and 25 are then loaded with sufficient nitrogen pressure that pressure gauges 24 and 26 readings are equal to the test pressure plus the pressure drop across the back pressure valve diaphragms.

The visual cell is pressurized by slowly and carefully opening main valve 15 followed by valve 21, after which the $CO_2$ is charged into the visual cell by admitting water to the upper side of the transfer vessel 10. This should be done gradually so that the pressure rise in the visual cell is not sudden. The cell pressurization is continued until the reading of visual cell pressure gauge 27 is equal to the desired test pressure. At this point, a predetermined volume of oil is injected by first opening oil valve 38 and shutting the $CO_2$ valve 15. For example, 5 ml. of oil is injected and the amount injected is determined from the pumping rate and the duration of injection and is verified by measuring the travel of the oil transfer vessel piston rod 50. A predetermined volume, for example, 50 ml., of the foamant solution is then injected at the bottom of the visual cell. This done by opening valves 42 and 16 and then shutting valves 38 and 21. Once the desired volume of foamant is injected, the $CO_2$ injection is resumed by opening valve 15 and shutting valve 44. The test is then continued in the same manner as described above.

Once the test is completed, the apparatus may be cleaned without depressuring the system by connecting valve 18 to a pump and injecting an appropriate solvent, such as toluene, followed by methanol, with final drying by nitrogen.

Foamants which are to be used for $CO_2$ injection processes may be evaluated in this way. However, foamants for use in processes which involve the injection of other gases including steam, air, nitrogen, flue or exhaust gas, natural gas, methane, ethane, propane, butane, liquefied petroleum gas and mixtures of these gases, may also be evaluated in the same way, using the appropriate gas in the test sequence.

I claim:

1. Apparatus for determining the foaming characteristics of a foamant for use in the recovery of oil from subterranean oil-bearing formations by gas flooding operations, under conditions simulating those in the formation, comprising:
   (i) a test cell containing a packing medium and having observation means for viewing the interior of the cell from the outside of the cell,
   (ii) a first inlet at the top of said cell through which the interior of the test cell is pressurized to a gas pressure simulating the reservoir pressure of said subterranean formation, and
   (iii) a second inlet air the bottom of said cell through which gas is passed into the packing medium in the cell in the presence of a liquid including the foamant at a predetermined flow rate.

2. Apparatus according to claim 1 in which both said first and second inlets are connected to a common gas pressure regulator so as to maintain the reservoir simulated pressure in said cell during the passage of gas into said cell through said second inlet.

3. A method for determining th foaming characteristics of a foamant to be used in the recovery of oil from a subterranean oil-bearing formation by gas flooding operations carried out in the presence of a flooding gas, comprising:
   (i) passing the gas to be used in the flooding operations through a porous medium in the presence of a liquid including the selected foamant, under pressure,
   (ii) determining the quantity of foam formed in a predetermined period of time and at a specified gas flow rate.

4. A method according to claim 3 which includes monitoring the pressure gradient along the direction of gas flow.

5. A method according claim 5 in which the gas is carbon dioxide.

6. A method according to claim 3 in which the porous medium comprises a porous medium simulating the formation.

7. A method according to claim 3 in which the porous medium comprises oil-wet glass spheres.

8. A method according to claim 3 in which the foamant comprises an aqueous solution of a surfactant.

* * * * *

UNITED STATES PATENT AND TRADEMARK OFFICE
CERTIFICATE OF CORRECTION

PATENT NO. : 4,589,276

DATED : May 20, 1986

INVENTOR(S) : N. F. Djabbarah

It is certified that error appears in the above-identified patent and that said Letters Patent is hereby corrected as shown below:

Col. 6, line 44, "dyying" should be --drying--.

Col. 8, line 42 (Claim 3), "th" should be --the--;

line 57 (Claim 5), "according claim 5" should read --according to claim 3--;

line 59 (Claim 6), after "according" insert --to--.

Signed and Sealed this
Seventh Day of October, 1986

[SEAL]

*Attest:*

DONALD J. QUIGG

*Attesting Officer*    *Commissioner of Patents and Trademarks*